United States Patent [19]

Briggs et al.

[11] 4,427,425
[45] Jan. 24, 1984

[54] SURGICAL DRAINAGE BAGS

[75] Inventors: Peter J. Briggs, Sompting; Steven Carpenter, Chichester, both of England

[73] Assignee: Matburn (Holdings) Limited, London, England

[21] Appl. No.: 436,724

[22] Filed: Oct. 26, 1982

Related U.S. Application Data

[63] Continuation of Ser. No. 248,860, Mar. 30, 1981, abandoned.

[30] Foreign Application Priority Data

Mar. 31, 1980 [GB] United Kingdom ............... 8010778
Feb. 27, 1981 [GB] United Kingdom ............... 8106228

[51] Int. Cl.³ ............................................. B01D 19/00
[52] U.S. Cl. ........................................ 55/159; 55/387; 604/333
[58] Field of Search ................. 55/158, 159, 316, 382, 55/387, 486, 528; 128/283; 210/446, 489, 490, 491, 502, 503, 505; 604/333

[56] References Cited

U.S. PATENT DOCUMENTS

| 1,411,975 | 4/1922 | Matson | 55/486 X |
|---|---|---|---|
| 2,544,579 | 3/1951 | Ardner | 128/283 |
| 2,555,086 | 5/1951 | Guinn | 128/283 |
| 3,439,677 | 4/1969 | Bonfils | 128/283 |
| 3,690,320 | 9/1972 | Riely | 128/283 |
| 3,778,971 | 12/1973 | Granger et al. | 55/159 |
| 3,804,091 | 4/1974 | Nolan et al. | 128/283 |
| 3,952,727 | 4/1976 | Nolan | 128/283 |
| 4,035,540 | 7/1977 | Gander | 128/283 X |
| 4,062,451 | 12/1977 | Gander | 128/283 X |
| 4,120,715 | 10/1978 | Ockwell et al. | 128/283 X |
| 4,181,513 | 1/1980 | Fukuda et al. | 55/316 |
| 4,203,445 | 5/1980 | Jessup et al. | 128/283 |
| 4,211,224 | 7/1980 | Kubach et al. | 128/283 |
| 4,232,672 | 11/1980 | Steer et al. | 128/283 |
| 4,268,286 | 5/1981 | Steer et al. | 128/283 X |
| 4,274,848 | 6/1981 | LaGro | 128/283 X |

FOREIGN PATENT DOCUMENTS 2730286 12/1978 Fed. Rep. of Germany .
2036564 7/1980 United Kingdom .
1596496 8/1981 United Kingdom .

Primary Examiner—Robert H. Spitzer
Attorney, Agent, or Firm—McAulay, Fields, Fisher, Goldstein & Nissen

[57] ABSTRACT

A filter for a surgical drainage bag has a filter layer of activated carbon cloth. Gases may pass through this filter layer from the interior of the bag. A first layer of gas permeable thermoplastics material is arranged in contact with the front side of the filter layer. A barrier layer of gas permeable hydrophobic material has its rear side in contact with the front side of the first layer. A second layer of gas permeable thermoplastics material has its rear side in contact with the front side of the barrier layer. All the various layers are secured together by a peripheral seal.

9 Claims, 3 Drawing Figures

SURGICAL DRAINAGE BAGS

This is a continuation of application No. 248,860 filed Mar. 30, 1981, now abandoned.

BACKGROUND OF THE INVENTION

Surgical drainage bags such as are commonly used by ileostomy or colostomy patients are often known as "ostomy" bags and that term will be used herein.

Ostomy bags commonly comprise two sheets of a flexible plastics material arranged in face contact and welded or otherwise secured at the edges. This produces a bag with two walls which are in face contact until the bag is filled. One of these walls, herein considered to be the rear wall, contacts the body of the patient when the bag is in use. The rear wall of such a bag has an inlet capable of receiving the stoma of a patient and the contents of the intestine of the patient can pass through this inlet into the interior of the bag. The contents flowing into the bag include flatus which would undesirably inflate the bag if it was not allowed to escape and for this purpose many such bags are provided with a vent through which these gases may pass. It is well known for this vent to include a deodourising filter which may, if desired, be constructed as described in our German Offenlegungsschrift Pulbication No. 2730286.9. However, the ability of such filters to pass gases freely depends on the pore size of the component parts. Thus, a filter that is sufficiently porous to allow a satisfactory flow of gas may well not prevent the transmission of liquid through the filter with the result that the filter tends to leak. The present invention seeks to overcome this disadvantage.

BRIEF SUMMARY OF THE INVENTION

A filter for a surgical drainage bag comprising a filter layer of activated carbon cloth through which gases may pass from the interior of the bag, a first layer of gas permeable thermoplastics material in contact with one side of the filter layer, a barrier layer of gas permeable hydrophobic material having one side in contact with the said first layer, a second layer of gas permeable thermoplastics material having one side in contact with the other side of the barrier layer, all the said layers being secured together by a peripheral seal. If desired, the said first layer of thermoplastics material may be in the form of a frame, such as a ring.

Activated carbon cloth is sometimes known as activated charcoal cloth.

The term "gas permeable hydrophobic material" as used herein is intended to mean a material which is substantially impervious to liquid discharged from the stoma of a patient and which preferably also allows adequate gas flow at a pressure of 150 millimeters of water or less.

In a modification at least one further layer of gas permeable thermoplastics material is arranged on the other side of the filter layer. Any such further layer of gas permeable plastics material (other than the outermost such layer) may be in the form of a frame, such as a ring.

BRIEF DESCRIPTION OF THE ACCOMPANYING DIAGRAMMATIC DRAWINGS

DESCRIPTION OF PREFERRED EMBODIMENTS

Figure 1:
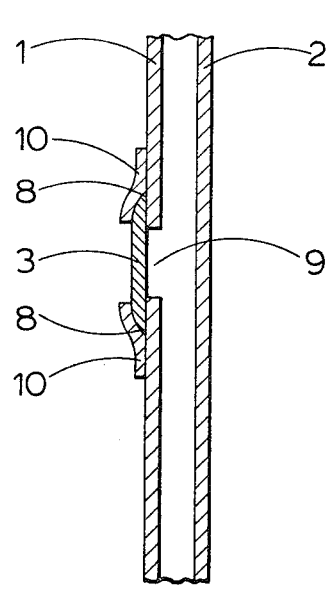
FIG. 1 is a sectional view of a portion of a surgical drainage bag.
Figure 2:
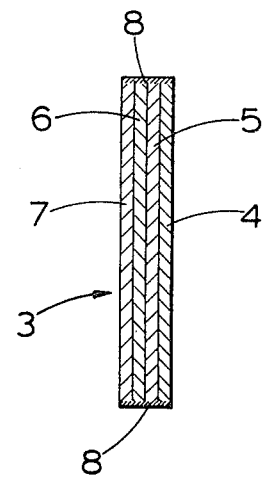
FIG. 2 is a sectional view of one embodiment of a filter of the bag.

In the embodiment of the invention illustrated in FIGS. 1 and 2 the ostomy bag is made of two sheets of flexible plastics material sealed together, for example by welding, at the perimeter edges of the bag. One of these walls is a rear wall 1 arranged to contact the body of a patient wearing the bag and the other wall is considered to be a front wall 2. The rear wall includes a vent 9 through which gases from the interior of the bag can pass. This vent incorporates a deodourising filter 3 which is located on the outside of the rear wall 1 of the bag.

One embodiment of the filter 3 is illustrated in FIG. 2 and comprises a layer 4 of carbon cloth which is the actual filter layer. Adjacent the filter layer 4 is a layer 5 of gas permeable thermoplastics material. In contact with the layer 5 is a barrier layer 6 which is also gas permeable and additionally hydrophobic. Finally, another layer 7, conveniently of the same material as the layer 5, is arranged on the outside of the layer 6. All of the layers are secured together by a peripheral seal 8 extending through the various layers.

The layer 5 can if desired be in the form of a ring or outer frame since it is only required as a vehicle for the peripheral seal 8.

The filter is arranged over the vent opening of the wall 1 preferably with the carbon cloth filter layer 4 innermost. The filter is secured to the bag using for example an adhesive ring 10.

The barrier layer 6 is preferably a layer of silicone-treated paper which is permeable to gas but impermeable to liquid, under normal conditions.

The layers 5 and 7 are either inherently gas permeable or are rendered gas permeable by perforations or at least one aperture. The layers 5 and 7 are also preferably liquid impermeable.

Figure 3:
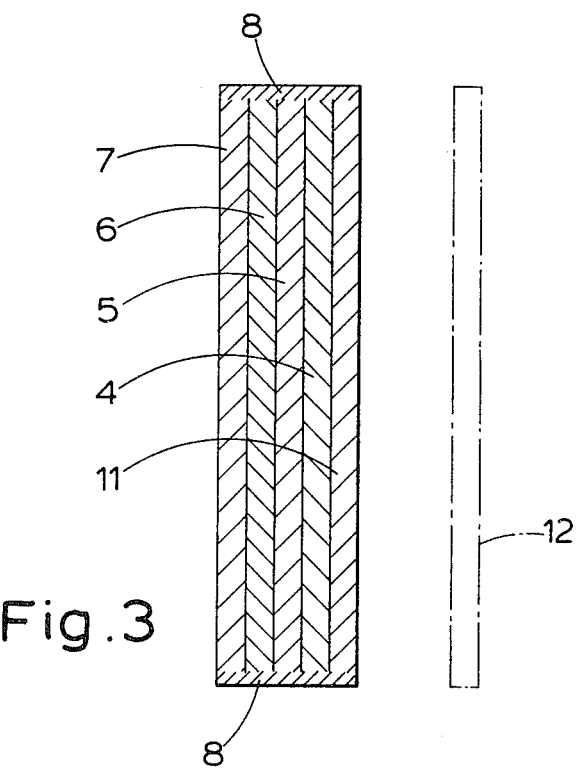
FIG. 3 is a sectional view of another embodiment of a filter of a bag.

In the embodiment illustrated in FIG. 3, a further or third layer 11 of the gas permeable thermoplastics material is arranged in contact with the other, or innermost surface of the filter layer 4.

In yet another embodiment, a still further or fourth layer 12 of gas permeable thermoplastics material illustrated in broken lines in FIG. 3 is arranged in contact with the third layer.

The layers 5, 7, 11 or 12 are preferably made of spun-bonded plastics material such as that known as "Tyvek" (Registered Trade Mark).

We claim:

1. A filter for a surgical drainage bag comprising a filter layer of activated carbon cloth through which gases may pass from the interior of the bag, a first layer of gas permeable thermoplastic material in contact with one side of the filter layer, a barrier layer of gas permeable hydrophobic material having one side in contact with said first layer, said hydrophobic material being constructed of a material that is substantially impervious to liquid discharged from a stoma and permitting adequate flow of gas at a pressure of 150 mm of water or less, a second layer of gas permeable thermoplastic material having one side in contact with the other side of the barrier layer, and a peripheral seal extending through all of said layers to secure together said layers.

2. A filter as claimed in claim 1, wherein at least one further layer of gas permeable thermoplastics material is arranged on the other side of the filter layer, and being secured thereto by said peripheral seal.

3. A filter as claimed in claim 1 wherein said first layer of gas permeable thermoplastics material is in the form of a ring or outer frame.

4. A filter as claimed in claim 1, wherein the barrier layer is of silicone-treated paper.

5. A filter as claimed in claim 1, wherein the layers of gas permeable thermoplastics material are of spun-bonded plastics material.

6. A filter as claimed in claim 1, wherein the layers of thermoplastics material are rendered gas permeable by at least one perforation.

7. A filter as claimed in claim 1, wherein a third layer of gas permeable plastics material is arranged with one side in contact with the other side of the filter layer and a fourth layer of gas permeable thermoplastics material is arranged in contact with the third layer and said peripheral seal extends through said third and fourth layers.

8. In a surgical drainage bag having a vent in a wall thereof, the improvements in which there is incorporated in said vent a filter comprising a filter layer of activated carbon cloth through which gases may pass from the interior of the bag, a first layer of gas permeable thermoplastics material in contact with one side of the filter layer, a barrier layer of gas permeable hydrophobic material having one side in contact with the said first layer, said hydrophobic material being constructed of a material that is substantially impervious to liquid discharged from a stoma and permitting adequate flow of gas at a pressure of 150 mm of water of less, a second layer of gas permeable thermoplastics material having one side in contact with the other side of the barrier layer, and a peripheral seal extending through all of said layers to secure together said layers.

9. A bag as claimed in claim 8, in which said filter is arranged with said filter layer inwards of said barrier layer.

* * * * *